United States Patent [19]

Bailey et al.

[11] Patent Number: 5,660,545

[45] Date of Patent: Aug. 26, 1997

[54] GEAR DRIVE FOR IMPLANT CONNECTOR

[75] Inventors: A. Gregory Bailey, Alabaster; A. C. Folsom, Jr., Pelham, both of Ala.

[73] Assignee: Crystal Medical Technology, a division of Folsom Metal Products, Birmingham, Ala.

[21] Appl. No.: 533,541

[22] Filed: Sep. 25, 1995

[51] Int. Cl.⁶ .................................................. A61C 8/00
[52] U.S. Cl. .................................................. 433/173; 433/174
[58] Field of Search .................................. 433/172, 173, 433/174, 175, 176, 177

[56] References Cited

U.S. PATENT DOCUMENTS 2,644,231  7/1953  Brennan ........................... 433/173
3,579,829  5/1971  Sampson .......................... 433/173
5,071,345  12/1991  Rosen ............................ 433/173 X
5,073,111  12/1991  Daftary .......................... 433/173

*Primary Examiner*—Nicholas D. Lucchesi
*Attorney, Agent, or Firm*—Veal & Associates

[57] ABSTRACT

An abutment for use in connecting a prosthesis to an implant member is provided with an opening in the rear wall thereof within which a pinion gear is mounted in a suitable rotational seal. The pinion gear is provided with a drive socket accessible from the exterior of the abutment such that the pinion gear may be rotated with an appropriate tool. The pinion gear is mated to a bevel gear formed on an annular flange of a retaining screw such that rotation of the pinion gear by the appropriate tool results in proportional rotation of the bevel gear. The retaining screw has a threaded portion and which engages an internally threaded portion of the implant member or of the abutment.

17 Claims, 2 Drawing Sheets

GEAR DRIVE FOR IMPLANT CONNECTOR

FIELD OF THE INVENTION

The present invention relates to medical technology and, more specifically, to prosthetic implantation of devices which are osseointegrated into bone. More particularly, the present invention relates to connectors used in such implants to secure a prosthesis to the implant which has been integrated into the bone. In even greater particularity, the present invention relates to an abutment connector which allows a threaded connection to the implant to be tightened from a direction transversely of the longitudinal axis of the implant. In even greater particularity, the present invention relates to an implant connector for dental prosthesis which allows the dental prosthesis to be placed on the implant without the necessity for an occlusal plug to cover the attachment means.

BACKGROUND

Medical implant history dates back at least to the last century. The widespread use of dental implants has only been practiced for the past twenty-five years. Dental implants, within the meaning used herein, refers to an assembly designed to replicate and replace a damaged or diseased tooth and its sub-endosseal structure.

Accordingly, the assembly includes an implant which is in effect an internally threaded socket which is inserted into a hole drilled into the bone of the jaw in position to support the assembly. This implant is osseointegrated into the bone and serves to anchor the prosthesis in the manner of the root of a tooth. An abutment structure rests atop the implant and provides connection between the implant and the dental prosthesis. These devices often employ threaded connections to fasten the components of the assembly together.

Common problems associated with the connection reported by practitioners relate to the screw retaining the prosthesis on the abutment, which is perpendicular to the occlusal surface of the prosthesis for axial engagement with the abutment or implant. As may be expected, the known prior art requires access to the screw through the occlusal surface of the prosthesis, necessitating a hole in the prosthesis. Obviously, after the retaining screw is appropriately tightened, the hole must be plugged or filled to prevent the accumulation of food particles within the prosthesis. It is a concern of the patient that the plug spoil the esthetics of the occlusal surface. A further concern is that the plugs are often unable to withstand the high stresses placed on the occlusal surfaces, thus necessitating an annoying repair of the prosthesis. Inasmuch as the plugs are difficult to fit properly, they are susceptible to stress failure and often result in poor hygienic conditions and poor esthetic conditions on the ocehsal surface. In some instances, extremely small screws and pins have been attempted; however, such devices are likely to fail with the deleterious effect of allowing the prosthesis to move freely or disengage. An alternative to the threaded connector has been to fit a one piece crown over the abutment. This practice is somewhat unsatisfactory in that the crown is often sacrificed or damaged if it has to be removed for any reason.

Accordingly, a need exists for a connection between the implant and prosthesis which will enhance the stability, sanitation, and stylishness of the prosthesis.

SUMMARY OF THE INVENTION

It is the principle object of the present invention to allow access to the retaining screw which secures an abutment/prosthesis assembly to an osseointegrated implant for the purpose of either removing or installing the assembly without damaging the occlusal surfaces of the prosthesis.

Another object of the invention is to improve the stability of the prosthesis as it is mounted in the implant.

Another object of the invention relative to dental implants is to improve the esthetic quality of the prosthetics use in such assemblies.

Still another object of the invention is to promote oral hygiene by reducing the likelihood of food entrapment in a prosthetic implant. Yet another object of the invention is to allow easy removal and replacement of the prosthesis for cleaning and repair.

These and other objects and features of the invention are accomplished by the unique combination of components and their interaction as more fully described herein. The foregoing objects are facilitated in the present invention by the ability of the practitioner to apply torque to the retaining screw at an angle to the centerline of the screw being torqued. Accordingly, the abutment in the present invention is provided with an opening in the rear wall thereof within which a pinion gear is mounted in a suitable rotational seal. The pinion gear is provided with a drive socket accessible from the rear of the abutment such that the pinion gear may be rotated with an appropriate tool. The pinion gear is mated to a bevel gear formed on an annular flange of the retaining screw such that rotation of the pinion gear by the appropriate tool results in proportional rotation of the bevel gear. The retaining screw has a threaded portion and which engages the internal threads of the implant or of the abutment. A greater appreciation of the invention will be obtained from a study of the following description in conjunction with the attached drawings.

BRIEF DESCRIPTION OF THE DRAWINGS

Apparatus embodying features of the invention are depicted in the appended drawings which form a portion of this disclosure and wherein.

DESCRIPTION OF THE PREFERRED EMBODIMENTS

Figure 1:
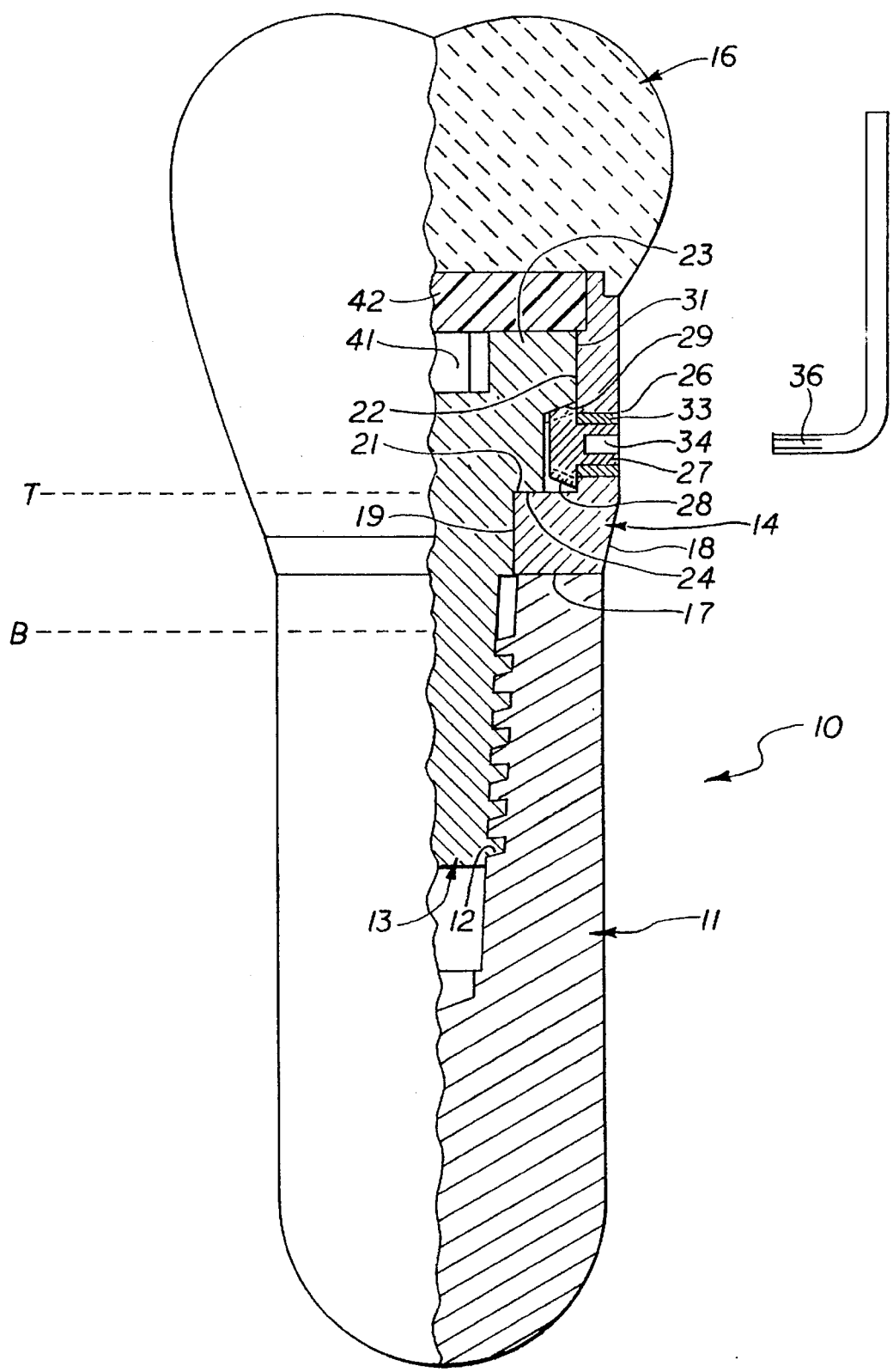
FIG. 1 is an elevational view partially in section showing the component parts of the implant assembly.

Referring to the Figures, it will be noted that the invention is depicted as a dental implant assembly; however, it will be appreciate that the invention may be employed in connection with other prostheses which admit access to the implant and abutment interface, for example a cosmetic soft tissue implant of the type used to remediate disfigured patients. Referring to FIG. 1, as will be understood, the assembly 10 includes an implant 11, which is shown generically in that the exact external configuration may vary depending on the preference of the surgeon. Internally, the implant is threaded as at 12 to threadedly engage a threaded portion of the shaft of a screw 13 which secures an abutment connection 14. The abutment 14 carries a prosthesis or crown 16 which may be affixed to the abutment 14 by a dental adhesive or glue or may be bonded to the abutment in any other acceptable manner. As will be noted from FIG. 1, the crown 16 extends to below the tissue line T on the front of the abutment 14 to achieve the proper esthetic appearance. However, the crown 16 does not extend significantly over the back side of the abutment 14.

Figure 2:
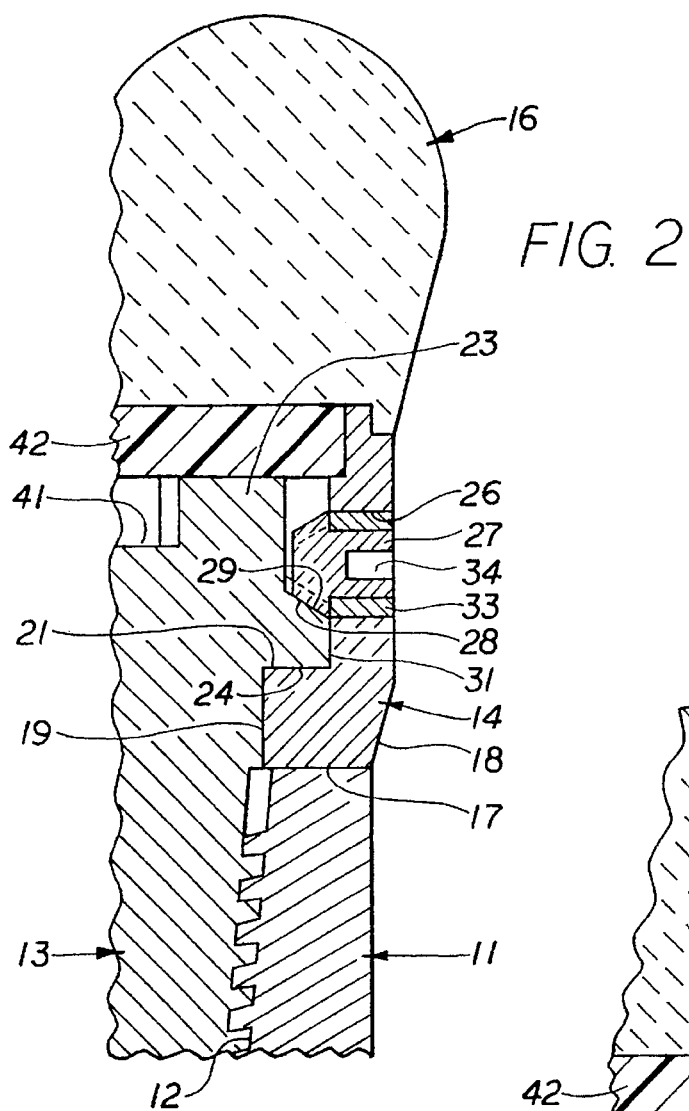
FIG. 2 is a partial elevational view of a second embodiment in section.

Abutment 14 is a cylindrical body having an annular bore extending therethrough with the bore having a number of stepped diameters. Abutment 14 is sized to mate at a first end 17 on the implant 11 just above bone level B, and may have an external conic section 18 to insure a matching external profile at the junction with implant 14. Internally, first end 17 has a bore portion 19 of sufficient diameter to accommodate passage of the threaded end of screw 13 therethrough to allow the shaft of the screw carrying threaded portion to engage the threads 12 of implant 11. A bearing surface 21 is formed intermediate bore portion 19 and a second bore portion 22 having a larger internal diameter. Screw 14 has a head 23 such that a thrust shoulder 24 is formed between the head and shaft of screw 13. The cylindrical wall of abutment 14 has an opening 26 formed on the backside subjacent the crown. Opening 26 receives a drive shaft 27 of a pinion gear 28 therethrough with the pinion gear carried inside second bore portion 22 in position to mate with a gear ring 29 which may be a conic gear formed on screw head 23. Pinion gear 28 and gear ring 29 form a bevel gear set. The term bevel gear set is intended to include straight bevel gears, zerol bevel gears, spiral bevel gears, coniflex straight bevel gears, hypoid gears, or angular gears. Gear ring 29 may be formed on the radius of the head 23 opposite thrust shoulder 24, as shown in FIG. 2, or may be formed on an annular flange 31 extending radially about head 23 as shown in FIG. 1. Head 23 may have an emergency removal socket 41 formed therein to facilitate removal of the screw and abutment in some untoward emergency. A seal plug 42 is positioned within second bore portion 22 or an enlargement thereof intermediate crown 16 and screw 13.

Opening 26 is formed such that pinion gear 28 is carried in mating relation to gear ring 29 in a heat sealed bearing 33 such that the bore of abutment 14 is sealed about drive shaft 27. Shaft 27 has a pinion drive socket 34 formed axially therein. A tool 36 having an end conforming to the socket is used by a dental practitioner to rotate the pinion gear 27 to torque screw 13 in engagement with implant 11. When the prosthesis is properly positioned and screw 13 is properly tightened the tool is removed and socket 34 is filled with a removable epoxy. If the implant assembly develops a problem or fails in some manner necessitating removal of the prosthesis for repair or the like, the epoxy can be removed with a dental instrument and the tool used to loosen screw 13 such that the abutment and crown may be removed.

It will be appreciated that once the crown is affixed to the abutment these components become unitary such that no relative motion therebetween occurs. Accordingly, the screw and pinion assembly would be positioned before the crown is affixed to abutment 14.

Figure 3:
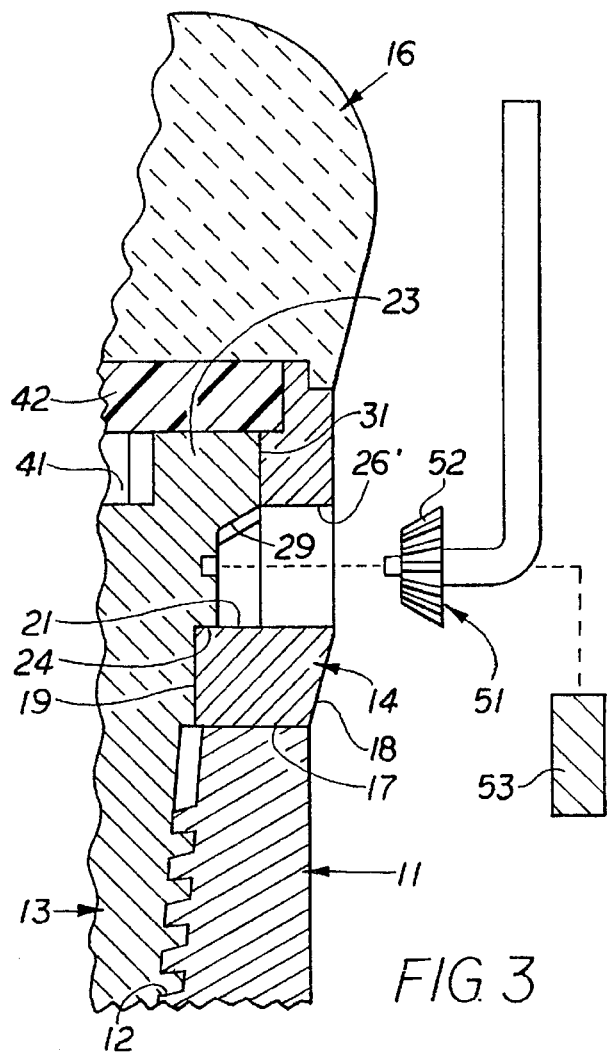
FIG. 3 is a partial sectional view of a third embodiment.

Referring to FIG. 3, it will be seen that an alternative embodiment employs a special tool 51 in the manner of a chuck, thereby eliminating internal pinion gear 24. This embodiment requires a slightly larger opening 26' to accommodate the tool pinion gear 52; however, it is considerably simpler to construct. The opening is sealed with a dental compound 53 subsequent to the placement of the implant and crown. As will be appreciated, the opening 26 may be formed to permit access to the gear 28 regardless of whether the gear is carried by a flange as in FIG. 1, or formed in the top of the screw 13.

From the foregoing, it may be seen that the prosthesis may be provided with an occlusal surface which has no defect due to the fabrication process inasmuch as the retaining screw is accessed on the back of the abutment rather than through the prosthetic occlusal surface. Accordingly, the esthetic, hygienic, and stability problem encountered in the prior art are substantially solved with the present invention, which may take any of the forms illustrated by the foregoing description or may take any form properly encompassed within the scope of the appended claims, the foregoing description being merely for description.

What we claim is:

1. Apparatus for use in reconstructive implant surgery comprising:

(a) a prosthesis;
   (b) an abutment affixed to said prosthesis having a second end adapted for mating abutment with an internally threaded endosseous implant;
   (c) an axial screw rotatably mounted within said abutment with a male thread thereon for engagement with said internally threaded endosseous implant; and,
   (d) drive means extending substantially transversely to said screw for imparting rotation to said axial screw relative to said abutment and prostheses such that said male thread engages said implant and urges said abutment against said implant.

2. Apparatus as defined in claim 1 wherein said drive means comprises means for translating rotational forces transverse of said axial screw into rotation of said screw.

3. Apparatus as defined in claim 1 wherein said drive means comprises a conic gear circumscribing said axial screw and a pinion gear engaging said conic gear for imparting concomitant rotation thereto, said pinion gear being mounted in said abutment and accessible laterally of said abutment to impart rotation thereto.

4. Apparatus as defined in claim 3 wherein said pinion gear comprises a shaft extending through a radial opening in said abutment and having an axial drive socket formed therein.

5. Apparatus as defined in claim 3 wherein said abutment comprises a cylindrical member having an annular shoulder formed therein intermediate a reduced internal diameter portion circumscribing said axial screw, and a normal diameter portion having a radial opening formed therein through which a shaft formed on said pinion gear extends.

6. Apparatus as defined in claim 5 wherein said axial screw comprises a shank portion having a first diameter, carrying said male thread, a thrust shoulder having a second diameter greater than said shank portion and less than said normal diameter portion of said abutment, and a flange extending radially of and axially spaced from said thrust shoulder and carrying said conic gear thereon such that said pinion gear is positioned intermediate said flange and said annular shoulder.

7. Apparatus as defined in claim 5 wherein said prosthesis comprises a dental crown affixed to said abutment and overlying said axial screw.

8. Apparatus as defined in claim 1 wherein said drive means comprises a conic gear circumscribing said axial screw and a pinion gear engagable with said conic gear for imparting concomitant rotation thereto, said pinion gear being mounted on a tool for selective engagement with said conic gear, through an opening formed in said abutment on a rear portion thereof, to impart rotation thereto.

9. Apparatus as defined in claim 8 wherein said abutment comprises a cylindrical member having an annular shoulder formed therein intermediate a reduced internal diameter portion circumscribing said axial screw, and a normal diameter portion having a radial opening formed therein through which said tool may be inserted to engage said conic gear.

10. Apparatus as defined in claim 9 wherein said axial screw comprises a shank portion having a first diameter, carrying said male thread, a thrust shoulder having a second diameter greater than said shank portion and less than said normal diameter portion of said abutment, and a flange extending radially of and axially spaced from said thrust shoulder and carrying said conic gear thereon such that said pinion gear is engagable therewith intermediate said flange and said annular shoulder.

11. Apparatus as defined in claim 9 wherein said axial screw comprises a shank portion having a first diameter, carrying said male thread, a thrust shoulder having a second diameter greater than said shank portion and carrying said conic gear thereon such that said pinion gear is engagable therewith superjacent said thrust shoulder.

12. Apparatus for affixing a dental prosthesis in the mouth of a patient wherein an internally threaded endosseous implant is affixed in the patient's mouth comprising:

(a) a cylindrical abutment having a first end for abutment with an endosseous implant and a second end for engagement with a dental prosthesis and a cylindrical wall intermediate said first and second ends;

(b) a threaded member adapted for axial rotation within said abutment for securing a prosthesis to said abutment; and, (c) means for imparting rotation to said threaded member through said cylindrical wall.

13. Apparatus as defined in claim 12 wherein said means for imparting comprises a bevel gear set including a drive gear mounted on a shaft extending through said cylindrical wall and a driven gear circumscribing said threaded member for concomitant driven rotation therewith.

14. Apparatus as defined in claim 13 wherein said shaft includes an axial drive socket for receiving a driving tool.

15. Apparatus as defined in claim 13 wherein said threaded member comprises a shank portion extending through said first end and having a male thread thereon and a head portion having a diameter greater that said shank portion such that an annular bearing surface is formed the therebetween and an annular flange extending radially from said head potion and carrying thereon said driven gear.

16. Apparatus as defined in claim 15 wherein said abutment has a first internal diameter within which said flange is received and a reduced diameter at said first end such that a bearing seat is formed therebetween in abutting relation to said bearing surface.

17. Apparatus as defined in claim 15 wherein said threaded member has formed therein an axial drive socket adapted to receive a driving tool for emergency removal of said abutment.

* * * * *